United States Patent [19]

Watanabe et al.

[11] Patent Number: 4,543,372

[45] Date of Patent: Sep. 24, 1985

[54] LOW DUSTING POWDERY ALGINATE IMPRESSION MATERIAL FOR DENTAL USE

[75] Inventors: Kazuhiro Watanabe, Kamifukuoka; Sakae Yoshikawa, Chofu; Shunichi Futami, Nagareyama, all of Japan

[73] Assignee: G-C Dental Industrial Corp., Tokyo, Japan

[21] Appl. No.: 664,963

[22] Filed: Oct. 26, 1984

[30] Foreign Application Priority Data

Nov. 2, 1983 [JP] Japan .............................. 58-204727

[51] Int. Cl.$^4$ .............................................. A61K 6/08
[52] U.S. Cl. ...................................... 523/109; 106/35; 106/206; 106/208; 106/209; 433/214; 524/28
[58] Field of Search .................. 523/109; 106/35, 206, 106/208, 209, 38.5 D; 524/28; 433/214

[56] References Cited

U.S. PATENT DOCUMENTS 4,468,484  8/1984  Pellico ................................ 523/109

Primary Examiner—Lorenzo B. Hayes

Attorney, Agent, or Firm—Oblon, Fisher, Spivak, McClelland & Maier

[57] ABSTRACT

A low dusting powdery alginate impression material for dental use is disclosed which comprises:

(a) an alginate,
(b) a gelling agent,
(c) a gelation controlling agent,
(d) a filler,
(e) at least one hydrophobic liquid having a vapor pressure of not higher than 3.15 mmHg at 20° C. selected from the group consisting of a hydrocarbon and a silicone oil not containing a hydrophilic group,
(f) polyvinylpyrrolidone, and
(g) at least one compound selected from the group consisting of oxides, hydroxides and fluorides of metals.

With the alginate impression material, gypsum models prepared using the negative mold of an impression have high surface precision and impressions of oral cavity having high precision can be obtained as well as substantially no dust formation is observed when taken out of a storage container and during mixing with water.

16 Claims, No Drawings

LOW DUSTING POWDERY ALGINATE IMPRESSION MATERIAL FOR DENTAL USE

BACKGROUND OF THE INVENTION

1. Field of the Invention

The present invention relates to alginate impression materials provided in the form of powder. More particularly, the present invention relates to alginate impression materials which are low dusting, are excellent storage stability and are capable of giving a gypsum model with high precision.

2. Description of the Prior Art

Generally, alginate impression materials for dental use which are provided in the form of powder are inexpensive and permit preparation of impressions of an oral cavity with appropriate precision and therefore they have heretofore been used widely. Upon use, a predetermined amount of a powdery alginate impression material for dental use (hereinafter referred to as "alginate impression material" for brevity) and water are placed in a small rubber bowl and mixed using a spatula to form a paste, which is then put on a tray for impression, and the tray is introduced into the oral cavity of a person and pressed onto his portion from which it is desired to copy an impression. After the paste has gelled to form an elastic material, it is taken out of the oral cavity, thus preparing an impression of the portion in the oral cavity. Then, a gypsum slurry is poured into the negative model of the impression and a gypsum model as a working model for preparing a prosthetic appliance is obtained. How the detail of the surface of the gypsum is reproduced determines adaptability of the prosthetic appliance prepared when it is put on in the oral cavity. The roughness of the surface of the gypsum model depends on the conditions of the interface between the alginate impression material and the material of the gypsum model.

Therefore, in practice, those materials which accelerate or do not inhibit gelation of alginate impression materials or congelation of gypsum must be chosen.

When mixed with water, alginate impression materials become a paste. Further, in order to form a homogeneous gel elastic body, the alginate impression material comprises fine powdery components and contains particularly fine powders of diatomaceous earth, silicic anhydride, talc, calcium carbonate, pearlite, etc., generally in an amount of 50 to 80% by weight.

Such conventional powdery alginate impression materials cause precipitation during storage and therefore the bulk density of the powder itself tends to change gradually with the lapse of time. For this reason, it is common practice that upon use, a container in which the alginate impression material is stored is shaken to agitate the content and cause the powders precipitated to regain the smallest possible bulk density, and thereafter a predetermined amount of the powder is gathered with precision using a spoon having a definite surface area exclusively used for this purpose. When a lid or cap of the container is removed after the shaking of the container, dust is scattered outside of the container airborne. Further, dust is also formed when a predetermined amount of the powder is mixed with water in a small rubber bowl due to the agitation by a spatula used. The dust formed not only is unpleasant to users but also causes environmental pollution and is harmful to health. These are disadvantages of the conventional alginate impression materials.

In order to solve the above problems attempts have been made as described in Japanese Patent Application Laid-open No. 57-501426 to coat fine powders of an alginate impression material with a coating agent which can be wetted with water easily and rapidly. Examples of the coating agent used in this process include a natural polymer dispersing agent such as xanthane rubber, sodium polyalginate, etc., a cellulose ester or ether such as hydroxylethylcellulose, carboxymethylcellulose, etc., a synthetic nonionic surface active agent derived from polyethylene glycol, polypropylene glycol, polyol, an alkanolamine, a glycerol ester. These substances contain in the molecule thereof a hydrophilic group such as —COOH, —OH, —NH$_2$, —CH$_2$, —CH$_2$O—, etc. and have an excellent wettability with water or a substitute liquid for water.

However, this process (Japanese Patent Application Laid-Open No. 57-501426) has disadvantages that water absorption of the alginate impression material is increased, resulting in that depolymerization if the alginate contained therein due to presence of water as well as reaction between alkaline components and acidic components is accelerated. Therefore, the quality of product is deteriorated rapidly and storage time or shelflife is shortened considerably.

Further, no reference is made in Japanese Patent Application Laid-open No. 57-501426 to precision of the surface of a gypsum model prepared from the impression material used. The coating agent described in this prior art inhibits or retards congelation of the gypsum and as a result a gypsum model prepared by pouring gypsum slurry into the negative mold of an impression has a rough surface, which leads to low precision.

A technology described in Japanese Patent Application No. 58-98021 filed by the same applicant aims at reducing dispersibility of dust and improving storage stability by coating the powder with a coating agent comprising a nonionic surface active agent and a hydrophobic liquid having a vapor pressure of not higher than 3.15 mmHg at 20° C. selected from hydrophobic liquid hydrocarbons, fatty acids, alcohols, oils, silicone, etc. However, this technology is not intended to smooth the surface of a gypsum model and improve the precision thereof.

Nonionic surface active agents do not inhibit gelation of alginate impression materials or congelation of gypsum. However, they are ineffective for smoothing the surface of a gypsum model prepared using an impression made of an alginate impression material containing the nonionic surface active agents. This is believed to be due to the fact that the nonionic surface active agent is not dissolved to form ions but is loosely bound with a great number of molecules of water through hydrophilic groups such as —OH, —O—, etc. and therefore hydration reaction of gypsum and subsequent growth of crystals of gypsum dihydrate during congelation will proceed relatively slowly, resulting in that crystals of gypsum dihydrate tend to grow easily.

SUMMARY OF THE INVENTION

An object of the present invention is to provide an alginate impression material which has a low dusting property.

Another object of the present invention is to provide an alginate impression material capable of giving smoothness and high precision to the surface of a gypsum mold prepared using an impression made of the material.

Still another object of the present invention is to provide an alginate impression material which shows improved storage stability.

As a result of extensive research it has now been found that the above objects and other objects which will be apparent from the following description can be attained by providing an alginate impression material composition containing at least one hydrophobic liquid having substantially no volatility and substantially little affinity with water, which is selected from a hydrocarbon and/or a silicone oil, and a small amount of polyvinylpyrrolidone in combination.

The present invention is based on the above finding, and provides a low dusting powdery alginate impression material for dental use, comprising such known components as (a) an alginate,
(b) a gelling agent,
(c) a gelation controlling agent,
(d) a filler, and other additives if necessary,
(e) at least one hydrophobic liquid having a vapor pressure of not higher than 3.15 mmHg at 20° C. selected from the group consisting of a hydrocarbon and a silicone oil not containing a hydrophilic group,
(f) polyvinylpyrrolidone, and
(g) at least one compound selected from the group consisting of oxides, hydroxides and fluorides of metals

DETAILED DESCRIPTION OF THE INVENTION

In the present invention, it is believed that one of the essential component, i.e., polyvinylpyrrolidone, is ionized and exhibits a catalytic effect in the acceleration of congelation of gypsum, which permits formation of fine crystals of gypsum dihydrate on the surface of gypsum in contact with the impression material. In addition, polyvinylpyrrolidone exhibit synergistic effect in the presence of an oxide, hydroxide or fluoride of a metal so that the surface of a gypsum model can further be smoothed, thus improving the precision of the gypsum model. As is known conventionally, use of the oxide, hydroxide or fluoride of the metal alone leads to the surface of gypsum at most as smooth as that obtained in Comparison Examples 1, 2 and 3 shown in Table hereinbelow, and no further improvement is obtained.

Although combination of Component (e), the hydrophobic liquid, with Components (a), (b), (c), (d) and (g) gives rise to a low dusting alginate impression material having an increased storage stability, this composition is unsatisfactory since it has a decreased mixability with water because of presence of Component (e), thus deteriorating processability or operability thereof. Use of polyvinylpyrrolidone, Component (f), adds to improvement in the processability, and endows the alginate impression material both a low dusting property and storage stability, and addition of at least one compound selected from the group consisting of oxides, hydroxides and fluorides of metals as component (g), together with polyvinylpyrrolidone, gives rise to synergistic effects to further improve the surface roughness of a gypsum model. A combination of hydrocarbon and/or silicone oil with polyvinylpyrrolidone is, inter alia, favoured, which is superior in precision of gypsum model, improved storage and low dusting property of the material.

In the alginate impression material of the present invention, any conventional alginates, gelling agents, gelation controlling agents, fillers and oxides, hydroxides and fluorides of metals can be used as Components (a), (b), (c), (d) and (g) respectively.

The alginate impression material, of the present invention can contain conventional additives such as pigments, perfumes.

Examples of the alginate which can be used as Component (a) include one or more of water soluble salts of alginic acid such as sodium alginate, potassium alginate, ammonium alginate, triethanolamine alginate, etc. These alginates can be used alone or in combination with each other.

Examples of the gelling agent which can be used as Component (b) include sparingly water-soluble divalent or polyvalent metal salts, preferably calcium sulfate dihydrate and/or hemihydrate. Mixtures of the salts can also be used.

Examples of the gelation controlling agent which can be used as Component (c) include one or more of sodium or potassium various phosphates, silicates or carbonates or in combination with each other.

Examples of the filler which can be used as Component (d) include one or more of fine particle powders of diatomaceous earth, silicic anhydride, talc, calcium carbonate, pearlite, etc. These fillers can be used alone or in combination with each other.

As Component (g), oxides of divalent or polyvalent metals such as zinc oxide, aluminum oxide, magnesium oxide, etc., hydroxides of divalent or polyvalent metals such as magnesium hydroxide, lead hydroxide, etc. and fluorides of metals such as potassium silicofluoride, sodium silicofluoride, potassium titanium fluoride, potassium fluoride, sodium fluoride, etc. can be used.

The liquid which can be used as Component (e) must have a vapor pressure of not higher than 3.15 mmHg at 20° C. and be hydrophobic, and is selected from hydrocarbons and silicone oils not containing a hydrophilic group. Examples of suitable hydrocarbons include squalane, squalene, liquid paraffin, dodecane, tridecane, nonylbenzene, decylbenzene, etc. Examples of suitable silicone oils not containing a hydrophilic group include dimethylpolysiloxane oil, methylphenylpolysiloxane oil, modified silicone oils, etc. The above liquids can be used alone or in combination with each other.

The amount of the hydrophobic liquid (Component (e)) is from 1 to 10% by weight, preferably from 1 to 5% by weight based on the total weight of the alginate impression material. When less than 1% by weight of the hydrophobic liquid is used, the resulting composition is ineffective for reducing dust formation and improving storage stability. On the other hand, when the amount of the hydrophobic liquid is more than 10% by weight, the hydrophobicity of the resulting composition is so high that the composition has low affinity with water and operability upon preparing a paste by mixing is poor.

The term "hydrophobic liquid" as used herein refers to a liquid having a solubility in water of not higher than 1.0% by weight at 20° C.

Of the hydrophobic liquids which can suitably used, nonane has the highest vapor pressure being 3.15 mmHg at 20° C. Hydrophobic liquids having a vapor pressure of higher than 3.15 mmHg at 20° C. are disadvantageous since they tend to volatilize and their content in the composition is apt to be lost during storage. Therefore, the hydrophobic liquid used in the present invention must have a vapor pressure of not higher than 3.15 mmHg at 20° C.

Polyvinylpyrrolidone, Component (f), which is also called "Povidone", "Polyvidonam" and "Polyvidone", is a polymer of 1-ethenyl-2-pyrrolidone. For examples, available polyvinylpyrrolidone include "Rubiscol K" (trade name for a product of BASF AG), "Kollidon" (trade name for a product of BASF AG), "PVP" (trade name for a product of GAF Co.), etc.

In the present invention, any polyvinylpyrrolidone having an average molecular weight ranging from 1,500 to to 1,100,000 can be used. Two or more polyvinylpyrrolidones having different average molecular weights can also be used in combination.

The amount of polyvinylpyrrolidone which can be used in the present invention is from 0.1 to 2% by weight, preferably 0.1 to 1% by weight based on the total weight of the alginate impression material.

When shaking the container for storage and mixing upon use the alginate impression material of the present invention forms substantially no dust, and therefore users can handle it without discomfort since there is no fear to cause environmental pollution or injure their health.

Furthermore, with the alginate impression material of the present invention, gypsum molds prepared using the negative mold of an impression have high surface precision and impressions having constant high precision can be obtained since the material retains high quality for a long period of time.

The present invention will be described in greater detail with reference to the following non-limitative examples. In the examples and comparative examples all parts are by weight unless otherwise indicated.

EXAMPLE 1

| Component | Amount |
| --- | --- |
| Sodium Alginate | 15 |
| Calcium Sulfate Dihydrate | 15 |
| Trisodium Phosphate | 2 |
| Diatomaceous Earth | 60 |
| Talc | 5 |
| Potassium Titanium Fluoride | 1 |
| Aluminum Oxide | 2 |
| Polyvinylpyrrolidone (molecular weight: 2,500) | 0.9 |

The above components were blended in a blender. While a further blending was continued, 8 parts of squalane was added dropwise to the mixture. The resulting powder (16 parts) and 40 parts of water were placed in a rubber bowl and mixed using a spatula. After 5 seconds from the start of the mixing, wetting of the powder with water was observed, and after 30 seconds homogeneous paste was obtained. During the mixing dust formation was not observed.

The surface of a gypsum model prepared using the negative mold of an impression was tested and 10 point average surface roughness calculated is 6.0 micrometer. The model felt smooth.

EXAMPLE 2

The procedures of Example 1 were repeated except that the polyvinylpyrrolidone (molecular weight: 2,500) was replaced by 0.2 part of polyvinylpyrrolidone (molecular weight: 1,100,000) and squalane was replaced by 6 parts of nonylbenzene. After 5 seconds from the start of mixing, wetting of the powder with water was observed, and after 25 seconds homogeneous paste was obtained. No dust formation was observed during the mixing.

The surface of a gypsum model prepared using the negative mold of an impression was tested, and 10 point average surface roughness calculated is 7.5 micrometers. The model felt smooth.

EXAMPLE 3

The procedures of Example 1 were repeated except that the polyvinylpyrrolidone (molecular weight: 2,500) was replaced by 0.5 part of polyvinylpyrrolidone(molecular weight: 40,000) and squalane was replaced by 3 parts of dimethylpolysiloxane and 3 parts of liquid paraffin. After 5 seconds from the start of mixing, wetting of the powder with water was observed, and after 30 seconds homogeneous paste was obtained. No dust formation was observed during the mixing.

The surface of a gypsum model prepared using the negative mold of an impression was tested and 10 point average surface roughness calculated is 6.5 micrometers. The model felt smooth.

EXAMPLE 4

| Component | Amount |
| --- | --- |
| Potassium Alginate | 15 |
| Calcium Sulfate Dihydrate | 15 |
| Trisodium Phosphate | 2 |
| Fine Particle Silicic Anhydride | 10 |
| Diatomaceous Earth | 40 |
| Pearlite | 10 |
| Potassium Silicofluoride | 1 |
| Zinc Oxide | 4 |
| Polyvinylpyrrolidone (molecular weight: 9,500) | 0.8 |

The fine silicic anhydride particles, diatomaceous earth and pearlite were first blended in a blender, and 2.5 parts of liquid paraffin was added dropwise to the mixture. Then, the rest components were added and the whole composition was mixed. The resulting powders (16 parts) and 40 parts of water were placed in a rubber bowl and mixed using a spatula. After 5 seconds from the start of the mixing, wetting of the powder with water was observed, and after 30 seconds homogeneous paste was obtained. During the mixing no dust formation was observed.

The surface of a gypsum model prepared using the negative mold of an impression was tested and 10 point average surface roughness calculated is 5.0 micrometers. The model felt smooth.

EXAMPLE 5

The procedures of Example 4 were repeated except that the polyvinylpyrrolidone (molecular weight: 9,500) was replaced by 0.6 part of polyvinylpyrrolidone (molecular weight: 49,000) and liquid paraffin was replaced by 5 parts of methylphenylsilicone oil. After 5 seconds from the start of mixing wetting of the powder with water was observed, and after 30 seconds homogeneous paste was obtained. No dust formation was observed during the mixing.

The surface of a gypsum model prepared using the negative mold of an impression was tested and 10 point average surface roughness calculated was 7.5 micrometers. The model felt smooth.

EXAMPLE 6

The procedures of Example 4 were repeated except that the polyvinylpyrrolidone (molecular weight: 9,500) was replaced by 0.3 part of polyvinylpyrrolidone (molecular weight: 70,000) and liquid paraffin was replaced by 4 parts of dimethylsilicone oil. After 7 seconds from the start of mixing, wetting of the powder with water was observed, and after 30 seconds homogeneous paste was obtained. No dust formation was observed during the mixing.

The surface of a gypsum model prepared using the negative mold of an impression was tested and 10 point average surface roughness calculated is 7.7 micrometers. The model felt smooth.

EXAMPLE 7

| Component | Amount |
| --- | --- |
| Sodium Alginate | 15 |
| Calcium Sulfate Dihydrate | 15 |
| Trisodium Phosphate | 2 |
| Diatomaceous Earth | 60 |
| Talc | 5 |
| Potassium Titanium Fluoride | 1 |
| Aluminum Oxide | 2 |
| Polyvinylpyrrolidone (molecular weight: 2,500) | 0.9 |
| Tinting Red | 0.05 |
| Spearmint | 0.2 |

The above components were blended in a blender. While a further blending was continued, 8 parts of squalane was added dropwise to the mixture. The resulting powder (16 parts) and 40 parts of water were placed in a rubber bowl and mixed using a spatula. After 5 seconds from the start of the mixing, wetting of the powder with water was observed, and after 30 seconds homogeneous paste was obtained. During the mixing dust formation was not observed.

The surface of a gypsum model prepared using the negative mold of an impression was tested and 10 point average surface roughness calculated is 6.2 micrometer. The model felt smooth.

EXAMPLE 8

The procedures of Example 1 were repeated except that the polyvinylpyrrolidone (molecular weight: 2,500) was replaced by 0.2 part of polyvinylpyrrolidone (molecular weight: 1,100,000) and squalane was replaced by 6 parts of nonylbenzene, 8 parts of calcium sulfate dihydrate was replaced by 8 parts of calcium sulfate hemihydrate and 1 part of talc was replaced by 1 part of calcium carbonate. After 5 seconds from the start of mixing, wetting of the powder with water was observed and after 25 seconds homogeneous paste was obtained. No dust formation was observed during the mixing.

The surface of a gypsum model prepared using the negative mold of an impression was tested, and 10 point average surface roughness caluculated is 7.7 micrometers. The model felt smooth.

EXAMPLE 9

The procedures of Example 1 were repeated except that the polyvinylpyrrolidone (molecular weight: 2,500) was replaced by 1.2 part of polyvinylpyrrolidone (molecular weight: 1,500) and squalane was replaced by 3 parts of dimethylpolysiloxane and 3 parts of liquid paraffin, 2 parts of sodium alginate was replaced by 2 parts of ammonium alginate and 0.3 part of trisodium phosphate was replaced by 0.3 part of sodium carbonate. After 5 seconds from the start of mixing, wetting of the powder with water was observed, and after 30 seconds homogeneous paste was obtained. No dust formation was observed during the mixing.

The surface of a gypsum model prepared using the negative mold of an impression was tested and 10 point average surface roughness calculated is 7.5 micrometers. The model felt smooth.

EXAMPLE 10

| Component | Amount |
| --- | --- |
| Potassium Alginate | 15 |
| Calcium Sulfate Dihydrate | 15 |
| Tripotassium Phosphate | 2 |
| Fine Particle Silicic Anhydride | 10 |
| Diatomaceous Earth | 40 |
| Pearlite | 10 |
| Potassium Silicofluoride | 1 |
| Zinc Oxide | 4 |
| Polyvinylpyrrolidone (molecular weight: 9,500) | 0.8 |

The fine silicic anhydride particles, diatomaceous earth and pearlite were first blended in a blender, and 2.5 parts of liquid paraffin was added dropwise to the mixture. Then, the rest components were added and the whole composition was mixed. The resulting powders (16 parts) and 40 parts of water were placed in a rubber bowl and mixed using a spatula. After 5 seconds from the start of the mixing, wetting of the powder with water was observed, and after 30 seconds homogeneous paste was obtained. During the mixing no dust formation was observed.

The surface of a gypsum model prepared using the negative mold of an impression was tested and 10 point average surface roughness calculated is 5.3 micrometers. The model felt smooth.

EXAMPLE 11

The procedures of Example 4 were repeated except that the polyvinylpyrrolidone (molecular weight: 9,500) was replaced by 0.6 part of polyvinylpyrrolidone (molecular weight: 49,000) and liquid paraffin was replaced by 5 parts of methylphenylsilicone oil, tripotassium phosphate was replaced by 3 parts of sodium silicate and zinc oxide was replaced by 2 parts of magnesium hydroxide. After 5 seconds from the start of mixing wetting of the powder with water was observed, and after 30 seconds homogeneous paste was obtained. No dust formation was observed during the mixing.

The surface of a gypsum model prepared using the negative mold of an impression was tested and 10 point average surface roughness calculated was 7.6 micrometers. The model felt smooth.

EXAMPLE 12

The procedures of Example 4 were repeated except that the polyvinylpyrrolidone (molecular weight: 9,500) was replaced by 0.4 part of polyvinylpyrrolidone in which consist of 0.2 part of polyvinylpyrrolidone (molecular weight: 7,000) and 0.2 part of polyvinylpyrrolidone (molecular weight: 4,000) and liquid paraffin was replaced by 4 parts of dimethylsilicone oil and 2 parts of potassium alginate was replaced by 2 parts of triethanolamine alginate. After 7 seconds from the start of mixing, wetting of the powder with water was observed, and after 30 seconds homogeneous paste was obtained. No dust formation was observed during the mixing.

The surface of a gypsum model prepared using the negative mold of an impression was tested and 10 point average surface roughness calculated is 7.9 micrometers. The model felt smooth.

Comparative Example 1

The procedures of Example 4 were repeated except that the polyvinylpyrrolidone was omitted and liquid paraffin was replaced by 3 parts of polyoxyethylene (20) sorbitan monolaurate described in Japanese Patent Application Laid-open No. 57-501426.

Comparative Example 2

The procedures of Example 4 were repeated except that the polyvinylpyrrolidone was replaced by 1 part of polyoxyethylene (20) sorbitan monolaurate described in Japanese Patent Application No. 58-98021.

Comparative Example 3

The procedures of Example 4 were repeated except that both the polyvinylpyrrolidone and liquid paraffin were removed. It took 15 seconds for the powder to be wetted with water. Dust formation was observed during the mixing.

Comparative Example 4

The procedures of Example 1 were repeated except that Potassium Titanium Fluoride and Aluminum Oxide were omitted.

The alginate impression materials obtained in the examples and comparative examples were tested on the Testing Specification No. 18 of the A.D.A.S. with respect to setting time, setting time after forced deterioration, compressive strength, compressive strength after forced deterioration, weight concentration of released dust and surface roughness of a gypsum model prepared using an impression made of the impression material. The results obtained are shown in Table below.

TABLE

| | SETTING TIME | SETTING TIME AFTER FORCED DETERIORATION | COMPRESSIVE STRENGTH ($Kg/cm^2$) | COMPRESSIVE STRENGTH AFTER FORCED DETERIORATION ($Kg/cm^2$) | REDUCTION IN COMPRESSIVE STRENGTH (%) | WEIGHT CONCENTRATION OF DUST* ($mg/m^3$) | SURFACE ROUGHNESS OF GYPSUM** (micrometer) |
|---|---|---|---|---|---|---|---|
| EXAMPLE | | | | | | | |
| 1 | 2 min | 2 min 10 sec | 8.5 | 8.0 | 5.9 | 1.15 | 6.0 |
| 2 | 2 min 10 sec | 2 min 10 sec | 8.8 | 7.6 | 13.6 | 1.36 | 7.5 |
| 3 | 2 min 10 sec | 2 min 20 sec | — | — | — | 1.28 | 6.5 |
| 4 | 2 min 20 sec | 2 min 40 sec | 9.1 | 8.1 | 10.9 | 1.24 | 5.0 |
| 5 | 2 min | 2 min 20 sec | 8.9 | 7.5 | 15.7 | 1.42 | 7.5 |
| 6 | 2 min 20 sec | 2 min 10 sec | — | — | — | 1.46 | 7.7 |
| 7 | 2 min | 2 min 10 sec | 8.3 | 7.9 | 5.0 | 1.20 | 6.2 |
| 8 | 2 min 10 sec | 2 min 10 sec | 9.7 | 8.5 | 12.4 | 1.35 | 7.7 |
| 9 | 2 min 20 sec | 2 min 30 sec | 7.5 | 6.8 | 9.3 | 1.30 | 7.5 |
| 10 | 2 min 20 sec | 2 min 40 sec | 9.0 | 8.2 | 8.9 | 1.27 | 5.3 |
| 11 | 1 min 50 sec | 2 min | 9.0 | 7.9 | 12.2 | 1.44 | 7.6 |
| 12 | 2 min 30 sec | 2 min 20 sec | 8.1 | 7.0 | 13.6 | 1.41 | 7.9 |
| Comp. Ex. | | | | | | | |
| 1 | 2 min 20 sec | 50 sec | 7.4 | 1.6 | 78.4 | 2.54 | 16.2 |
| 2 | 2 min 10 sec | 2 min 20 sec | 8.0 | 7.0 | 12.5 | 1.15 | 15.5 |
| 3 | 2 min 30 sec | 4 min 10 sec | 8.5 | 3.5 | 58.8 | 29.12 | 12.3 |
| 4 | 3 min | 3 min 10 sec | 6.5 | 6.0 | 7.7 | 1.16 | 31.1 |

Notes:
*Weight Concentration of Dust: Sample (150 g) was placed in a round metal cylinder (diameter: 150 mm, length: 135 mm) with a cap. Immediately after the cylinder was shaked 5 times at a rate of 1 stroke per second the cap was removed and dust released from the surface of the sample was measured for 1 minute using a digital dust counter P-3 Model (Shibata Kagaku Co., Ltd.) and the weight concentration was obtained.
**Surface Roughness of Gypsum Model:
(1) Method: JIS B0601
(2) Apparatus: Surfcon 30 B (Tokyo Seimitsu Co., Ltd.)
Impression with a mirror surface was made using an alginate impression material, and gypsum slurry was poured into the negative mold of the impression and allowed to congeal at a relative humidity of 100%. After 1 hour, the gypsum model was separated from the impression, and measurements were conducted after 1 day.

From the results shown in the above Table, it can be seen that the alginate impression material obtained in Comparative Example 1 showed a considerable fluctuation in the setting time after forced deterioration and a considerable reduction time in the compressive strength. On the contrary, the alginate impression material of the present invention led to much less adverse effect when subjected to forced deterioration, and the amount of dust formed could be minimized. Furthermore, the gypsum model prepared using the negative mold of an impression made of the impression material of the present invention had an excellent surface smoothness and exhibited high performance as compared with those prepared using the negative molds of the impressions made of the respective impression materials obtained in Comparative Examples 1, 2, 3 and 4.

While the present invention has been described in detail and with reference to specific embodiments thereof, it will be apparent to one skilled in the art that various changes and modifications can be made therein without departing from the spirit and scope thereof.

What is claimed is:

1. In a powdery alginate impression material for dental use, comprising:
   (a) an alginate,
   (b) a gelling agent,
   (c) a gelation controlling agent,
   (d) a filler,
   (e) at least one compound selected from the group consisting of oxides, hydroxides and fluorides of metals, the improvement comprising:
   (f) at least one hydrophobic liquid having a vapor pressure of not higher than 3.15 mmHg at 20° C. selected from the group consisting of a hydrocarbon and a silicon oil not containing a hydrophilic group, and
(g) polyvinylpyrrolidone.

2. The material as claimed in claim 1, further comprising a pigment, a perfume or a mixture thereof.

3. The material as claimed in claim 1, wherein said hydrocarbon is selected from the group consisting of squalane, squalene, liquid paraffin, dodecane, tridecane, nonylbenzene and decylbenzene.

4. The material as claimed in claim 1, wherein said silicone oil is selected from the group consisting of dimethylpolysiloxane oil, methylphenylpolysiloxane oil and modified silicon oils.

5. The material as claimed in claim 1, wherein the amount of said hydrophobic liquid is from 1 to 10% by weight based on the total weight of the material.

6. The material as claimed in claim 1, wherein said polyvinylpyrrolidone is a polymer of 1-ethenyl-2-pyrrolidone that has an average molecular weight of 1,500 to 1,100,000.

7. The material as claimed in claim 1, wherein the amount of said polyvinylpyrrolidone is from 0.1 to 2% by weight based on the total weight of the material.

8. The material as claimed in claim 1, wherein said alginate is a water soluble salt of alginic acid selected from the group consisting of sodium alginate, potassium alginate, ammonium alginate and triethanolamine alginate.

9. The material as claimed in claim 1, wherein said gelling agent is a sparingly water-soluble divalent or polyvalent metal salt selected from the group consisting of calcium sulfate dihydrate, calcium sulfate hemihydrate and mixtures thereof.

10. The material as claimed in claim 1, wherein said gelation controlling agent is selected from the group consisting of phosphates, silicates and carbonates of sodium and potassium.

11. The material as claimed in claim 1, wherein said filler is selected from the group consisting of diatomaceous earth, silicic anhydride, talc, calcium carbonate and pearlite.

12. The material as claimed in claim 1, wherein said oxide of metal is selected from the group consisting of zinc oxide, aluminum oxide, and magnesium oxide.

13. The material as claimed in claim 1, wherein said hydroxide of metal is selected from the group consisting of magnesium hydroxide and lead hydroxide.

14. The material as claimed in claim 1, wherein said fluoride of metal is selected from the group consisting of potassium silicofluoride, sodium silicofluoride, potassium titanium fluoride, potassium fluoride and sodium fluoride.

15. The material of claim 1, wherein the oxides of metal comprise oxides of polyvalent metals.

16. The material of claim 1, wherein the hydroxides of metal comprise hydroxides of polyvalent metals.

* * * * *